United States Patent
Fernandes Da Cunha Vaz et al.

[11] Patent Number: 6,013,034
[45] Date of Patent: Jan. 11, 2000

[54] OCULAR FLUOROMETER

[76] Inventors: José Guilherme Fernandes Da Cunha Vaz, Centro de Oftalmologia da Universidade de Coimbra-HUC; José Paulo Pires Domingues; Carlos Manuel Bolota Alexandre Correia, both of Departmento de Fisica da Universidade de Coimbra, all of P-3000 Coimbra, Portugal

[21] Appl. No.: 08/968,883

[22] Filed: Nov. 5, 1997

Related U.S. Application Data

[63] Continuation of application No. 08/387,823, filed as application No. PCT/PT94/00005, Jun. 17, 1994, abandoned.

[30] Foreign Application Priority Data

Jun. 18, 1993 [PT] Portugal .................... 101290

[51] Int. Cl.$^7$ ......................................... A61B 6/00
[52] U.S. Cl. .................... 600/476; 351/214; 600/310
[58] Field of Search ............................... 600/310, 473, 600/475, 479, 477, 558, 398; 356/337, 338, 343; 250/574; 351/214, 216, 219, 221, 233

[56] References Cited

U.S. PATENT DOCUMENTS

| | | | |
|---|---|---|---|
| 4,019,813 | 4/1977 | Cornsweet et al. | 351/14 |
| 4,412,543 | 11/1983 | Vassiliadis et al. | 128/665 |
| 4,573,778 | 3/1986 | Shapiro | 351/219 |
| 4,761,071 | 8/1988 | Baron | 351/212 |
| 5,020,891 | 6/1991 | Lichtman et al. | 350/527 |

FOREIGN PATENT DOCUMENTS

| | | |
|---|---|---|
| 0512518 A1 | 11/1992 | European Pat. Off. . |
| 3117699 A1 | 10/1982 | Germany . |
| WO93/05699 | 4/1993 | WIPO . |
| WO93/20743 | 10/1993 | WIPO . |

OTHER PUBLICATIONS

Archives of Ophathalmology, vol. 101, No. 11, pp. 1753–1756, Nov. 1983.
Investigate Ophthalmology & Visual Science, vol. 29, No. 8, pp. 1285–1293, Aug. 1988.

*Primary Examiner*—Brian L. Casler
*Attorney, Agent, or Firm*—Morey B. Wildes; Cowan, Liebowitz & Latman, P.C.

[57] ABSTRACT

The instrument is to be adapted to an ophthalmic slit-lamp (2,6) and includes holders for fluorescence excitation and barrier filters (3,5) to the light path and a detector system made of a linear array of photodiodes (8) with respective circuitry for reading and control. The light is focused in a chosen zone of the eye (13) inducing fluorescence by using specific wavelength. The fluorescence is measured by the detector (8) coupled to one of the eyepieces (12) of the slit-lamp (26) or to a beam-splitter (7) placed before the eyepieces (12). There is a system for digitalization of the signal from the detector (8) which is connected to an IBM compatible computer (11) where the data is stored and analyzed.

8 Claims, 2 Drawing Sheets

OCULAR FLUOROMETER

This application is a continuation of application Ser. No. 08/387,823, filed Feb. 17, 1995, now abandoned filed as PCT /PT 94 /00005, Jun. 17, 1994 now abandoned.

BACKGROUND

This invention is a new ocular fluorometer.

The instrument is to be adapted to an ophthalmic slit-lamp 1 and includes holders for fluorescence excitation and barrier filters 3,5 in the light path and a detector system made of a linear array of photodiodes 8 with respective circuitry for reading and control 9. The light is focused in a chosen zone of the eye 13 inducing fluorescence by using specific wavelengths. The fluorescence is measured by the detector 8 coupled to one of the eyepieces of the slit-lamp 1, or to a beam splitter 7 placed before the eyepieces.

There is a system for digitalization of the signal from the detector which is connected to an IBM compatible computer 11 where the data is stored and analyzed.

The instrument has a spatial resolution of 50 $\mu$ (corresponding to the spacing between the photodiodes) and a sensitivity (lower level of detection) equivalent to the fluorescence of a fluorescein solution of 1 ng/mg. The excellent reproducibility and linearity of the instrument and its design are particularly appropriate for performing the most sophisticated ocular fluorometry measurements in the clinical ophthalmological practice, including studies of permeability of the blood-retinal barrier.

The present invention regards a new ocular fluorometer. The instrument is based on an ophthalmic slit-lamp using specific pairs of fluorescence excitation and barrier filters in the light path and a detector system made by a photodiode linear array with respective circuitry for reading and control. The incoming light from the slit is focused in the eye location where it is desired to measure the induced fluorescence. This in turn is measured using a detector system placed in one of the eyepieces of the slit-lamp microscope or using a beam splitter, the other eyepiece being used for focusing. There is also a system for digitalization of the signal from the detector which is connected to an IBM compatible computer where the data is stored and analyzed.

DESCRIPTION OF PRIOR ART

Since 1975, when the technique of vitreous fluorophotometry was proposed for the first time, as a method designed to measure low concentrations of fluorescein in the eye, and more specifically, in the vitreous body, different ocular fluorometers have been proposed.

The ocular fluormeters presently available have serious limitations. Among them:
- instrument dedicated optically to posterior segment examination
- fixed angle of measurement
- automatic scanning of the whole axis of the eye
- fixed filter system dedicated only to fluorescein detection This equipment is described in detail in: Early Breakdown of the Blood-Retinal Barrier in Diabetes, Jose G. Cunha-Vaz, J. R. Faria de Abreu, Antonio J. Campos and Grabiela M. Figo, British Journal of Ophthalmology, volume 59, n°. 11, pages 649–656, November 1975;—Vitreous Fluorophotometry for clinical research, Ran C. Zeimer, Norman P. Blair, Jose G. Cunha-Vaz, Arch. Ophthalmol, vol. 101, pages 1753–1756, November 1983; A Scanning Ocular Spectrofluorophotometer, Jay W. Mclaren and Richard F. Brubaker, Investigative Ophthalmology & Visual Science, vol., 29, n°. 8, pages 1285–1292, August 1988.

SUMMARY OF THE INVENTION

The fluorometer herein described solves the technical problems referred previously and minimizes costs of production. It is an instrument to be adapted to an ophthalmic slit-lamp 1 (a biomicroscope using slit illumination) where excitation and barrier filters 3,5 have been placed in the light path and a detector based on an array of photodiodes 8 with respective driver and readout circuits 9 which are standard in the field and are known to those of ordinary skill in the art. The illumination slit 4 is focused in the eye location 13 where the induced fluoresence is to be measured. This measurement is performed by a detector placed in one of the eyepiece of the slit-lamp; the other eyepiece is used for focusing. The equipment includes also a system for digitalization of the signal from the detector which is connected to a IBM compatible computer where the data is stored and analyzed.

One of the objectives of the invention is the conception of an instrument that is an accessory for adaptation to an ordinary ophthalmic slit-lamp. The new instrument is compact and more flexible for examination in various locations in the eye and not dedicated for posterior segment analysis.

Another objective is the possibility of utilization using different angles of measurement. The instrument proposed is based on another original concept: it has a system that allows automatic or manual positioning in selected areas of the eye of major clinical interest, such as the cornea/aqueous, aqueous/lens and vitreous/retina interfaces, performing electronic scanning in each of these areas.

It is, therefore, possible to obtain with this new system improved resolution and more rapid positioning in the areas of clinical interest.

Another objective of the invention is the possibility of quick changing of filters, both excitation and barrier. Such a device allows for detection of both exogenous and endogenous fluorescence, i.e., autofluorescfence of ocular tissues.

This instrument also offers, when compared to the ocular fluorometers available, excellent computational capabilities.

Finally, this invention involves production costs which are calculated as at least four times less than that of available instrumentation.

BRIEF DESCRIPTION OF THE DRAWINGS

For information and, therefore, without imposing undue restrictions we include two drawings (FIG. 1 and FIG. 2).

Figure 1:
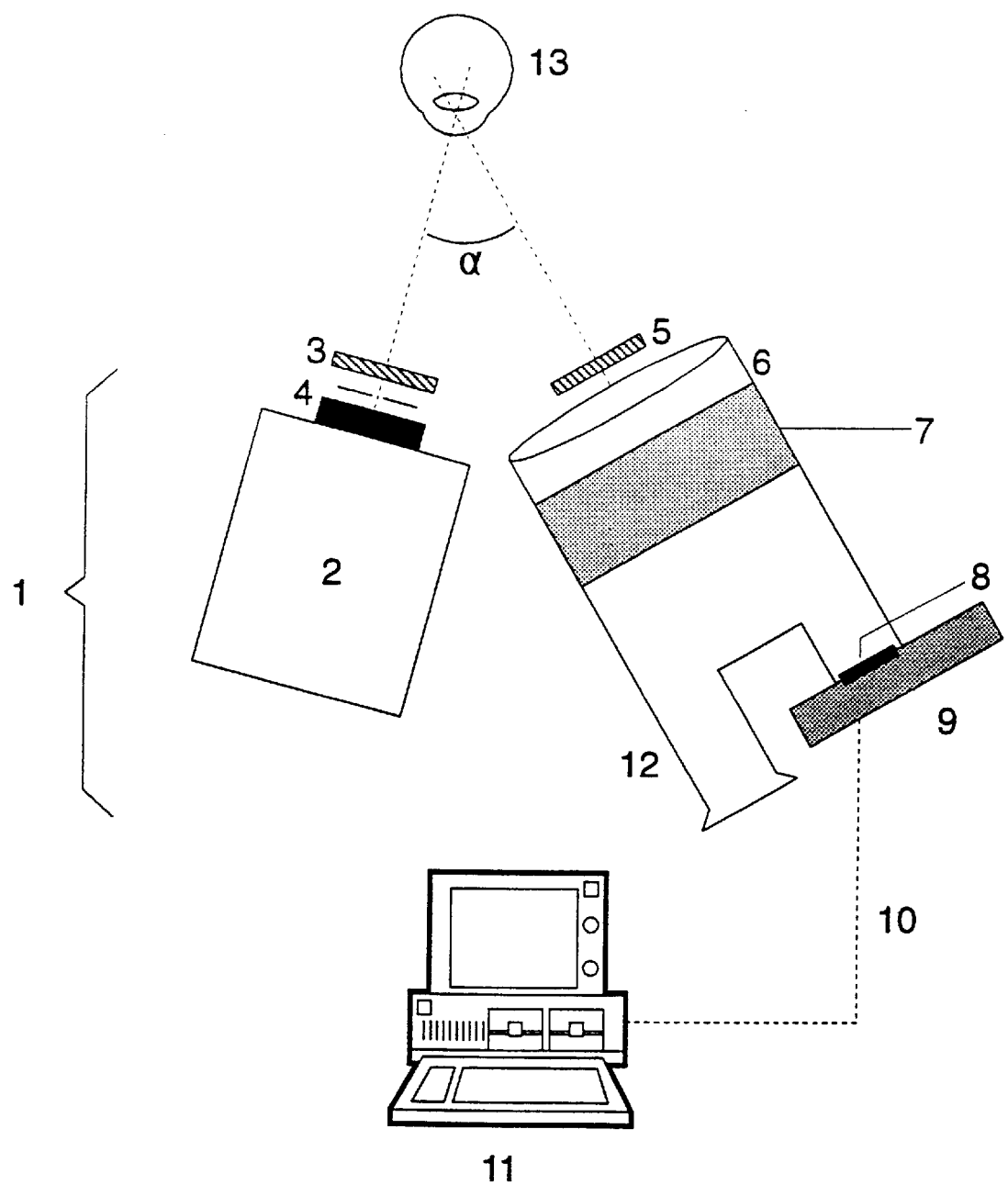
FIG. 1 shows schematically the ocular fluorometer.

Legend to FIG. 1:
1. Slit lamp;
2. Excitation lamp;
3. Excitation filters;
4. Slit;
5. Emission barrier filters;
6. Objective;
7. Modified beam-splitter;
8. Photodiode array;
9. Detector control board;
10. 50-way flat cable;
11. IBM PC compatible computer;
12. Oculars; and
13. Patient eye.

DETAILED DESCRIPTION OF A SELECTED SOLUTION

The invention is a fluorometric accessory to be adapted to an ophthalmic slit-lamp (biomicroscope with slit illumination) which is an equipment that is present in every ophthalmic examination room.

The fluormetric accessory must be coupled and installed without difficulties, must allow the use of the slit-lamp when not in use for ocular fluorometry and must allow flurometic measurements to be performed with high precision, reproducibility and reliability, competing in its technical performance with the best existing ocular flurometers available.

The conditions are, therefore:

1st Easy installation of the unit, easy coupling and uncoupling to an ordinary ophthalmic slit-lamp without the need of a specialized technician.

2nd Allow normal use of the slit-lamp when the fluorometric accessory is in place, without major hindrance.

3rd Perform fluorometric measurements at the level of the cornea, anterior chamber, lens, vitreous and retina with the required resolution and reliability.

4th Easy interchange and placement of new filter pairs in order to be able to measure exogenous and endogenous flurophores.

5th Perform flurometric measurements in a reproducible manner with the sensitivity and linearity at least comparable to instrumentation available in the market.

In order to fulfill these conditions the conception of the instrument took into consideration:

1st—Adaptation to the optical plane of the more distant eyepiece of the binocular system of the slit-lamp.

2nd—No interference with the optical system of the slit-lamp.

3rd—Good resolution, even better than in presently available instrumentation.

A photodiode array with a resolution between detectors of 50 μm was chosen. This corresponds "in vivo" to a resolution of 0.5 mm in the cornea-aqueous and aqueous-lens interfaces. This resolution is obtained using a measurement angle of 45°.

The instrument has the capacity of measuring in various angles, which opens its fields of application for specular and light scattering examination of the ocular structures. These different angles may also be kept constant if so desired, in order to maintain measurement reproducibility.

This instrument also performs separate and successive measurements in the cornea, lens and retina.

The existing alternatives to perform fluorometric measurements in different locations of the eye were based either on the capacity for mechanical automatic scanning along the axis of the eye or on isolated measurements in restricted areas of the eye (with the extent of measurements depending on resolution density of photodetectors).

Recognizing the limitation associated both with scanning of the entire eye, increasing the duration of the examination and resulting in a variety of artifacts and problems with eye fixation, and with examination of only restricted areas of the eye, this invention provides an original option for measurement based on the average size of the human eye.

Three zones of measurements are chosen: cornea, lens, and retina, the eye being approximately 24 mm long. This distance as well as the location of the anterior surfaces of the cornea, lens and retina may be determined experimentally using their specular reflection.

It was possible to develop a mechanical system 14 for positioning by automatic control using three main positions: Cornea (I), lens (II) and retina (III) using a common mechanical device for slit-lamp carriage displacement.

After the initial focusing step on the anterior surface of the lens, the examiner only has to press positioning button I in order to focus in the cornea. By pressing button III the detection system will be brought into focus on the retinal region, and, in this instance, it is also necessary to change the instrumentation angle between incident light and collected light angle to 14°, using a contact lens or special 60D lens.

In these conditions it is possible to obtain fluormetric measurements characterised by very good resolution in the areas of principal clinical significance (cornea-aqueous, aqueous-lens and vitreous-retina interfaces).

The fluorescence peaks obtained in the recordings performed before administration of any exogenous fluorophore indicate the autofluorescence of the cornea, lens and retina and serve as references when reading the results. The photodiode array is rotatable so as to act also in a spot fluorometer way, that is all detector elements contribute to measure the same eye location.

FIG. 1 shows the ocular fluorometer composed essentially by a module for excitation 2, a module for detection 6,9, a module for reading and control 9, a processing module and a computer 11 which are the electronic component of the instrument.

The module of excitation is composed essentially by a slit-lamp with device to receive appropriate excitation filters 3,5.

The electronics of the instrument starts at the detector chip 9 and ends at the computer 11 following the usual block diagram of any data acquisition and control systems, including:

(1) Transducer (2) Transducer readout circuit (3) Transducer driver and control circuit (4) Analogue to digital converter ("ADC").

For direct control of measurements and for data processing, the invention includes:

(5) A DSP based PC processor module, capable of running a local program, for data pre-processing and storage and direct control measurements (6) A computer, running simultaneously a second program, for general supervision, disk storage and graphical analysis of results.

(7) The photodetector is a solid state Self-Scanning Linear Photodiode Array from Hamamatsu, series S3921/S3924. It offers high performance and good flexibility and all the members of the series are pin compatible. This kind of sensor features an integrated signal processing circuit providing and output signal with a boxcar waveform thus allowing signal readout with a simple external circuit. Low dark current, large spectral range, good sensitivity and pixel pitch 50 μm (S3921) are some other important characteristics (see Hamamatsu MOS Linear Image Sensors for more technical details).

(8) Driver/Readout circuit. The driver circuit provides all the clock and control signals needed for the sensor to work properly (see technical data from Hamamatsu) with the timing parameters adjusted to the experiment requirements. The main part of this circuit is the software programmable Intel 8254 Timer. The readout circuit includes signal conditioning, amplification and quantification by the ADC (BURR BROW;N AD 7800). There is a clear interconnection between control and readout as the conversion timing of the ADC must be synchronized with sensor driving determining the pulse output frequency and width.

The sensor exposure time is determined by the overall timing of the Driver/Readout circuit.

(9) PC Module. This is a DSP (Digital Signal Processing) board containing the Texas Instruments TMS320C25 digital signal processor and was specially developed for this Ocular Fluorometer. It is to be plugged in a free slot of an ordinary PC compatible computer 11 and is connected to the detector module 9 (located at the ocular eye 12 end of the slit-lamp 1) by a 50-way flat cable 10. It has local memory accessed by both the TMS and the PC processor 11. It drives the sensor module and reads the converted data in a "stand alone" mode. It also performs some data pre-processing using some software noise reduction algorithms like arithmetic averaging. An important element of this module is the before referred 8254 Timer programmable by the PC but gated by the TMS which allows for acquisition timing maximum flexibility- one of the key features of the Instrument.

The Computer 11 is the interface between the user and the system. It gives the user the possibility of defining a friendly environment some of the measurements parameters. After the acquisition starts, the computer reads the pre processed data and we can follow on the monitor, in real time, the acquisition results and decide whether the data is to be stored on disk for posterior analysis. We can also introduce some correction factors to compensate for eventual non-uniformities and/or non-linearities. Finally the user can utilise the program for post-processing and to analyse data that has been stored on disk.

Figure 2:
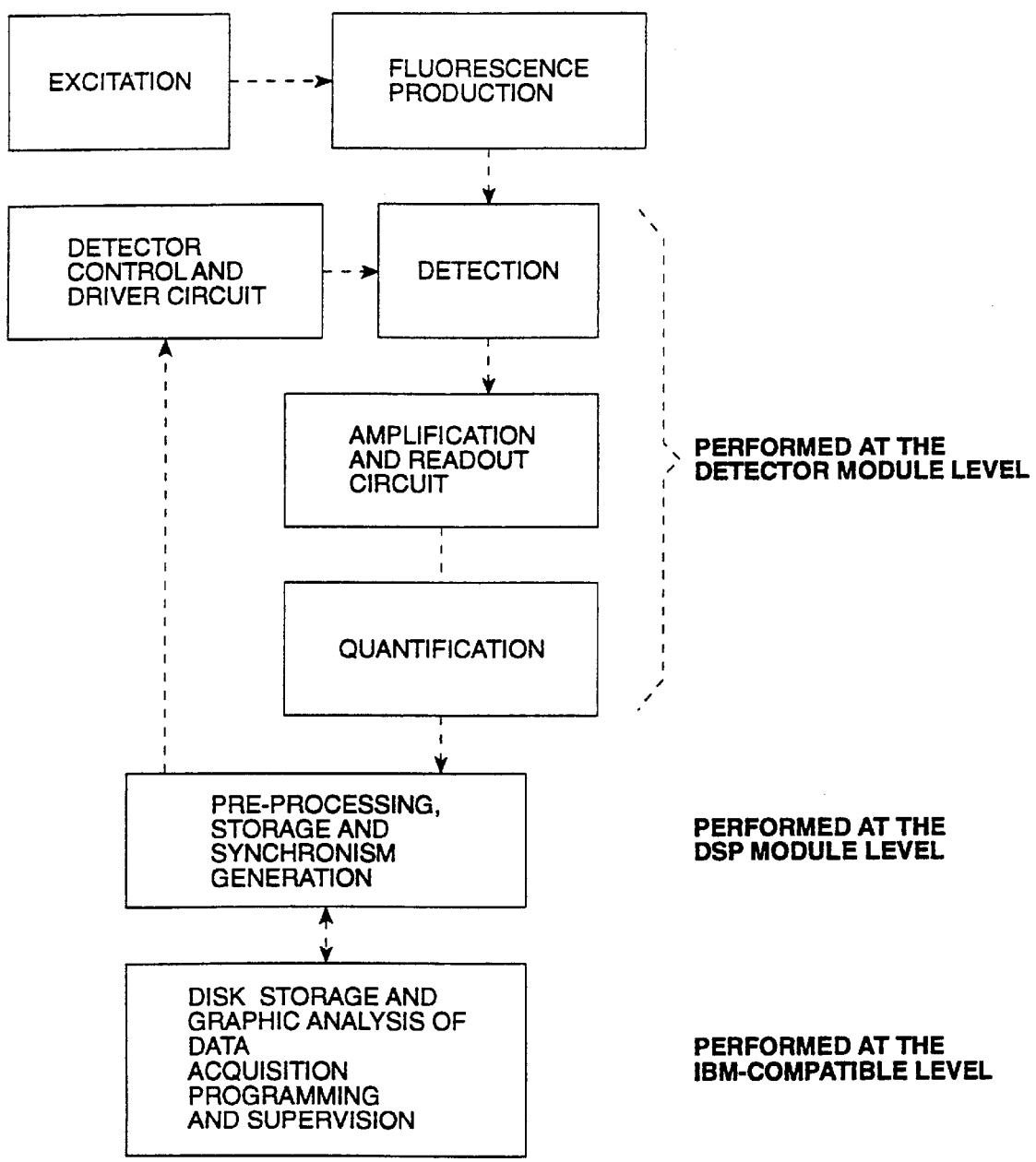
FIG. 2 shows the acquisition process block diagram.

In FIG. 2 the acquisition process block diagram is presented summarizing the function of the instruments and stating which models are responsible for them.

This description is not intended to be a complete one and some minor modification are possible and may be introduced. This invention should be considered limited only by the claims that follow.

We claim:

1. An Ocular Fluorometer for determining the concentration of fluorescent material in the eye, comprising an ordinary ophthalmic slit-lamp optical system having a beam-splitter, to which are adapted a filter for selecting excitation wavelength and a filter that functions to pass the fluorescence and to attenuate light scattering, and an electronic component coupled to one port of the beam-splitter, without interfering with the optical system of the slit-lamp and allowing its simultaneous normal use, that include a multiple photodiode detector for measuring specifically selected regions of the eye, reading and control circuits, and a computing means for control of measurement, storage and graphic analysis of the photometric results.

2. The Ocular Fluorometer according to claim 1 further comprising a mechanical device which allows for automated positioning in three main positions of focusing, centered respectively on the anterior surface of the cornea, anterior surface of the lens and retina-vitreous interface, comprising means for manually focusing by an examiner of the slit-lamp on the anterior surface of the lens; and means for positioning and automatically focusing on the area of the cornea or the vitreous-retina interface;

wherein said slit lamp is manually focused by an examiner on the anterior surface of the lens and then automatically focused on both the anterior surface of the cornea and, by manually varying the instrument angle and by introducing said accessory lens into the light path, on the retina-vitreous interface.

3. The Ocular Fluorometer according to claim 1 further comprising a linear array of photodiodes, respective driver and readout circuits for providing clock and control signals and for signal conditioning, amplification and quantification and controlled by a DSP that maximizes the ADC data rate in order to drastically reduce noise, whereby the photodiodes detect the fluorescent light from an area in focus, allowing high resolution fluorescence measurements.

4. The Ocular Fluorometer according to claim 3, wherein said photodiode array has a pixel-to-pixel spacing corresponding to an ultimate limit in spatial resolution of 50 $\mu$m and a Lower Level of Detection of 1 ng/ml fluorescein equivalent concentration.

5. The Ocular Fluorometer according to claim 3 wherein said computing means comprises processing means and memory means coupled to a host computing means, for driving a detector module of said Ocular Fluorometer, for reading converted data, for performing data pre-processing such as arithmetic averaging, and for assuring efficient connection to the host computing means for control of measurement, data storage and analysis, and graphical interface with a user.

6. The Ocular Fluorometer according to claim 5 further comprising two programs running simultaneously, one at the host computing means level and the other at the local processing means.

7. The Ocular Fluorometer according to claim 3, wherein said photodiode array is rotatable so as to act as both spot fluorometer and scanning fluorometer, a feature that is particularly important in the anterior chamber measurements.

8. An Ocular Fluorometer for determining the concentration of fluorescent material in specifically selected regions of special interest in the eye, comprising an ordinary ophthalmic slit-lamp optical system with a beam-splitter, filters for excitation and emission wavelength selection, an electronic component including a multiple photodiode detector, and state-of-the-art knowledge reading and control circuits for signal readout, and computing means for measurement control, storage and graphical analysis of the photometric results, wherein said multiple photodiode detector is entirely dedicated to measurements in each of the specifically selected regions to achieve high spatial resolution measurements crucial for blood-ocular barriers permeability assessment.

* * * * *